United States Patent [19]
Fujiwara et al.

[11] 3,940,383
[45] Feb. 24, 1976

[54] STREPTOZOTOCIN ANALOGS

[75] Inventors: Allan N. Fujiwara, Sunnyvale; Edward M. Acton; David W. Henry, both of Menlo Park, all of Calif.

[73] Assignee: Stanford Research Institute, Menlo Park, Calif.

[22] Filed: Dec. 12, 1974

[21] Appl. No.: 531,887

[52] U.S. Cl. .......... 260/210 R; 260/211 R; 424/180
[51] Int. Cl.² ..................... C07H 5/06; C07H 15/02
[58] Field of Search ...................... 260/210 R, 211 R

[56] References Cited
UNITED STATES PATENTS 3,767,640   10/1973   Suami et al. ..................... 260/210 R

*Primary Examiner*—Johnnie R. Brown
*Attorney, Agent, or Firm*—Donovan J. De Witt

[57] ABSTRACT

New 3-methyl-3-nitrosoureido derivatives of the following amino sugars were prepared as analogs of streptozotocin with the anomeric carbon protected, by nitrosating the methylureas in water with $N_2O_3$: 3-amino-3-deoxy-1,2-O-isopropylidene-α-D-ribofuranose; methyl 3-amino-3-deoxy-β-D-xylopyranoside; methyl 3-amino-3-deoxy-α-D-altropyranoside; methyl 3-amino-3-deoxy-α-D-glucopyranoside; and methyl 3-amino-2,3,6-trideoxy-α-L-lyxohexopyranoside. Tests against murine leukemia L1210 show that the anticancer activity of streptozotocin not only was retained but was enhanced in most of these derivatives.

6 Claims, No Drawings

STREPTOZOTOCIN ANALOGS

ORIGIN OF INVENTION

The invention described herein was made in the course of or under contract with the Department of Health, Education and Welfare.

BACKGROUND OF INVENTION

The subject matter of this application is described in detail in a publication by applicants which appears in *Journal of Medicinal Chemistry*, 17, 392 (1974). The matter disclosed in this publication is expressly incorporated by reference in the present application.

SUMMARY OF INVENTION

The present invention relates to the provision of five novel streptozotocin analogs which are useful in the treatment of leukemia L1210. These compounds may be termed the "3-methyl-3-nitrosoureido derivatives of the following amino sugars":

Methyl 3-amino-3-deoxy-β-D-xylopyranoside (see compound I below)
Methyl 3-amino-3-deoxy-α-D-altropyranoside (see compound II below)
3-Amino-3-deoxy-1,2-O-isopropylidene-α-D-ribofuranose (see compound III below)
Methyl 3-amino-2,3,6-trideoxy-α-L-lyxohexopyranoside (see compound IV below)
Methyl 3-amino-3-deoxy-α-D-glucopyranoside (see compound V below)

The five compounds of the present invention are identified below by name, chemical structure, Roman numeral and accession number (NSC) of the National Cancer Institute. A particular method of preparation for each of the compounds is set forth below in Examples 1–5, said example numbers coinciding with the Roman numerals (I–V) given herein to the particular compounds.

In the publication referenced above, the compounds I, II, III, IV and V are identified as compound Nos. (4), (11), (7), (21) and (15), respectively.

Methyl 3-Deoxy-3-(3-methyl-3-nitrosoureido)-β-D-xylopyranoside

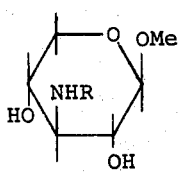

NSC 153365

R = CONCH$_3$
    |
    NO

I.

Methyl 3-Deoxy-3-(3-methyl-3-nitrosoureido)-α-D-altropyranoside

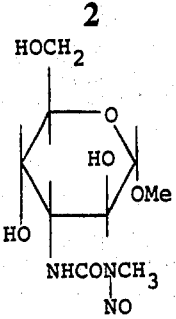

NSC 156273    II.

3-Deoxy-1,2,-O-isopropylidene-3-(3-methyl-3-nitrosoureido)-α-D-ribofuranose

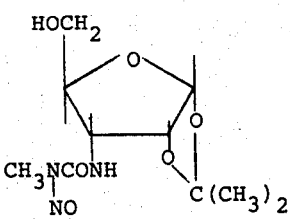

NSC 155692    III.

Methyl 2,3,6-Trideoxy-3-(3-methyl-3-nitrosoureido)-α-L-lyxohexopyranoside

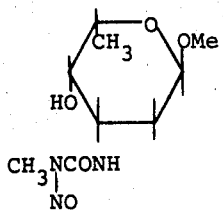

NSC 166643    IV.

Methyl 3-Deoxy-3-(3-methyl-3-nitrosoureido)-α-D-glucopyranoside

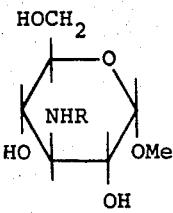

NSC 160466

R = CONCH$_3$
    |
    NO

V.

In all the above structural formulae the open valencies are attached to hydrogen.

In Examples 1 through 5 given below, detailed information is provided as to the method for preparing each of the compounds of the present invention, together with data as to the characteristics of each of said compounds.

EXAMPLE 1

Methyl 3-Deoxy-3-(3-methyl-3-nitrosoureido)-β-D-xylopyranoside (I)

Methyl 3-deoxy-3-(3-methylureido)-β-D-xylopyranoside.

Methyl 3-amino-3-deoxy-β-D-xylopyranoside (6.4 g, 40 mmoles), R. E. Schaub and M. J. Weiss, *J. Amer. Chem. Soc.*, 80, 4683 (1958); C. D. Anderson, L. Goodman and B. R. Baker, ibid., 80, 5247 (1958), was dissolved in 36 ml of water and chilled to 0°. To the cold stirred solution was added 2.6 ml (44 moles) of methyl isocyanate, in three portions, E. J. Hessler and H. K. Jahnke, *J. Org. Chem.*, 35, 245 (1970). The reaction mixture was stirred at 0° for 1 hour, at room temperature for 1 hour, filtered, and concentrated to a white solid. Recrystallization from ethanol/ethyl acetate (2:3) gave 7.5 g (85%) of crystalline solid, mp 179–181.5°; ir ($\mu$): 3.0 (NH,OH), 6.1 (C=O), 6.55 (amide II); nmr ($\delta$) (DMSO-$d_6$): 2.58 d (N—$CH_3$, 3H), 3.38 s ($OCH_3$, 3H), 4.15 d (H—1, 1H); tlc: methanol/benzene (1:1), $R_f$ 0.8.

Calcd for $C_8H_{16}N_2O_5$: C, 43.63; H, 7.32; N, 12.7. Found: C, 43.69; H, 7.18; N, 12.7.

Methyl 3-Deoxy-3-(3-methyl-3-nitrosoureido)-β-D-xylopyranoside.

Methyl 3-deoxy-3-(3-methylureido)-β-D-xylopyranoside (4.4 g, 20 mmoles) was dissolved in 35 ml of water and chilled to 0°. To the cold stirred solution was added 2.0 ml (2.9 g, 38.2 mmoles) of liquid dinitrogen trioxide, E. J. Hessler and H. K. Jahnke; *J. Org. Chem.*, 35, 245, (1970), whereupon a permanent positive test with starch iodide paper (purple color) was obtained. After stirring the reaction solution at 0° for 4 hours, lyophilization gave a gummy solid. The solid was dissolved in 40 ml of dichloromethane, dried over magnesium sulfate, and filtered. To the filtrate was added 9 ml of ether. After standing overnight at 0°, the crystalline product was collected and air dried to give 3.1 g (62%), mp 123°–124° dec. (evolution of gas); ir ($\mu$): 2.9 (NH, OH), 5.9 (C=O), 6.4 (amide II), 6.7 (NO); nmr ($\delta$) ($CDCl_3$): 3.18 s (N—$CH_3$, 3H), 3.52 s ($OCH_3$, 3H), 4.68 d(H-1, 1H, $J_{1,2}$=3.5 Hz); tlc: $R_f$ 0.4.

A water solution was stable, even to sonication, for at least 2 hours.

Calcd for $C_8H_{15}N_3O_6$: C, 38.55; H, 6.07; N, 16.9. Found: C, 38.22; H, 6.15; N, 16.7.

On a larger scale, 30 g (0.136 moles) of the urea was treated with 7 ml (0.136 moles) of $N_2O_3$ to yield after two lyophilizations 34.5 g (95%), mp 112–112.5, as the monohydrate. The solid could be stored at room temperature for a least 20 months, with no detectable change.

EXAMPLE 2

Methyl 3-Deoxy-3-(3-methyl-3-nitrosoureido)-α-D-altropyranoside (II)

Methyl 4,6-O-benzylidene-3-deoxy-3-(methylureido)-α-D-altropyranoside.

Methyl 3-amino-3-deoxy-4,6-O-benzylidene-α-D-altropyranoside, W. H. Myers and G. J. Robertson; *J. Amer. Chem. Soc.*, 65, 8 (1943), (8.4 g, 30 mmoles) was dissolved in 40 ml of tetrahydrofuran/water (5:3) and chilled to 0°, and then 2.0 ml (35 mmoles) of methylisocyanate added in one portion. The reaction mixture was stirred at 0° for 1.5 hour and at room temperature for 1 hour. It was filtered, and concentrated to a white foam weighing 9.5 g (93%); ir ($\mu$): 2.95 (NH, OH), 6.05 (C=O), 6.4 (amide II), 13.25 and 14.3 (aryl); nmr ($\delta$), ($CDCl_3$) 2.65 d ($NCH_3$, 3H), 3.38 s ($OCH_3$, 3H), 4.65 s (H-1, 1H), 5.52 s ($C_6H_5CH$, 1H); tlc: $R_f$ 0.7.

Calcd for $C_{16}H_{22}N_2O_6$: C, 56.79; H, 6.55; N, 8.28. Found: C, 56.53; H, 6.75; N, 8.48.

Methyl 3-deoxy-3-(3-methylureido)-α-D-altropyranoside. A solution of methyl 4,6-O-benzylidene-3-deoxy-3-(3-methylureido)-α-D-altropyranoside (7.1 g, 21 mmoles) in 150 ml tetrahydrofuran/water (3:7) and 20 g of Dowex resin (H) 50X-8 (50–100 mesh) (prewashed with THF and water) was stirred at room temperature for 5.5 hours and then filtered. The resin was washed with a little water and THF, combined with the reaction filtrate and concentrated to a glass to give 4.6 g (88%) of crude product; ir ($\mu$): 2.95 (OH, NH), 6.05 (C=O), 6.4 (amide II); nmr ($\delta$) (DMSO-$d_6$): 2.58 s ($NCH_3$, 3H), 3.32 s (—$OCH_3$, 3H), 3.4–4.1 m (H-2, H-3, H-4, H-5, H-6, 6H), 4.48 d (H-1, 1H); tlc: $R_f$ 0.25.

Calcd for $C_9H_{18}N_2O_6$: C, 43.19; H, 7.25; N, 11.2. Found: C, 42.98; H, 7.32; N, 11.3.

Methyl 3-Deoxy-3-(3-methyl-3-nitrosoureido)-α-D-altropyranoside.

Methyl 3-deoxy-3-(3-methylureido)-α-D-altropyranoside (4.4 g, 17.6 mmoles) was nitrosated as previously described in Example 1. After lyophilization, the solid residue was pulverised and dried in vacuo at 40° for 6 hours to give an analytically pure product; 4.5 g (91%), mp 116°–117°. The product was also recrystallized from ethanol (mp 117.5°–118°) without change in spectral properties; ir ($\mu$): 2.95, 3.1 (OH, NH), 5.8 (C=O), 6.6 (NO); nmr ($\delta$) ($D_2O$): 3.15 s ($NCH_3$, 3H), 3.42 s ($OCH_3$, 3H); tlc: $R_f$ 0.45.

Calcd for $C_9H_{17}N_3O_7$: C, 38.71; H, 6.14; N, 15.1. Found: C, 38.48; H, 6.07; N, 15.2.

The product was stable and remained unchanged in water at room temperature for at least 2 weeks. The solid could be stored at room temperature for at least 18 months, with no detectable change.

EXAMPLE 3

3-Deoxy-1,2-O-isopropylidene-3-(3-methyl-3-nitrosoureido)-α-D-ribofuranose (III)

3-Deoxy-1,2-O-isopropylidene-3-(3-methylureido)-α-D-ribofuranose.

3-Amino-3-deoxy-1,2-O-isopropylidene-α-D-ribofuranose, A. N. Fujiwara, E. M. Acton, and L. Goodman, *J. Heterocyclic Chem.*, 7, 891 (1970), (3.8 g, 20 mmoles) in water was treated with methyl isocyanate to give upon recrystallization from ethanol/ethyl acetate (1:3) 3.1 g (64%) of product, mp 162°–164°; ir ($\mu$): 3.0–3.1 d (OH, NH), 6.05 (C=O), 6.4 (NH); nmr ($\delta$) ($CDCl_3$): 1.45 s and 1.55 s [—$C(CH_3)_2$ 6H], 2.8 d (—$NCH_3$, 3H), 4.65 t (H-2 1H, $J_{1,2}$ 4 Hz), 5.87 d (H-1, 1H, $J_{1,2}$ 4 Hz); tlc $R_f$ 0.4.

Calcd for $C_{10}H_{18}N_2O_5$: C, 48.77; H, 7.37; N, 11.4. Found: C, 49.03; H, 7.28; N, 11.4.

3-Deoxy-1,2-O-isopropylidene-3-(3-methyl-3-nitrosoureido)-α-D-ribofuranose.

3-Deoxy-1,2-O-isopropylidene-3-(3-methylureido)-α-D-ribofuranose was nitrosated as previously described for two hours at 0° and then at room temperature for 1.5 hours. The reaction mixture was neutralized with Dowex 2X-8 ($CO_3$ form) to pH 6 and lyophilized to leave a pale yellow hygroscopic gum, 4.4 g (95%), that was analytically pure. In further processing, a solution of the product in methylene chloride was dried over magnesium sulfate; concentrated to a pale yellow syrup at 35°–40°; and crystallized by triturating with ether/petroleum ether (30°–60°) mixture, 3.0 g (64%), mp 88.5°–89.5°; ir ($\mu$): 2.9 (OH), 3.1 (NH), 5.85 (C=O), 6.5 (amide II), 6.75 (NO); nmr ($\delta$) ($CDCl_3$): 1.35 s and 1.55 s [$C(CH_3)_2$, 6H], 3.18 s (N—$CH_3$, 3H), 3.9 s (H-5, 2H), 5.95 d (H-1, 1H), tlc: $R_f$ 0.6.

Calcd for $C_{10}H_{17}N_3O_6 \cdot \frac{1}{4} H_2O$: C, 42.93; H, 6.31; N, 15.0. Found: C, 43.15; H, 6.36; N, 15.0.

A solution in chloroform was stable at room temperature up to three weeks, but the product decomposed slowly in water, and rapidly in dimethylsulfoxide. The solid, however, could be stored at room temperature for 19 months with no detectable change.

EXAMPLE 4

Methyl 2,3,6-trideoxy-3-(3-methyl-3-nitrosoureido)-α-L-lyxo-hexopyranoside (IV)

Methyl 2,3,6-trideoxy-3-methylureido-α-L-lyxo-hexopyranoside.

Methyl 2,3,6-trideoxy-3-amino-α-L-lyxo-hexopyranoside, J. P. Marsh, C. W. Mosher, E. M. Acton and L. Goodman; Chem. Commun., 973 (1967), (7.6 g, 47 mmoles) in water was treated with methyl isocyanate for 2¾ hours, and the product was recrystallized from hot water to give 6.2 g (61%), mp 191°–192°; ir ($\mu$): 2.75 2.9, 3.0 (NH, OH), 6.05 (C=O), 6.35 (amide II); tlc: $R_f$ 0.4; nmr ($\delta$) ($D_2O$): 1.23 d ($CCH_3$, 3H, $J_{5,6}$ 6.5 Hz), 1.65–2.0 m (H-2, 2H), 2.75 s ($NCH_3$, 3H); 3.4 s ($OCH_3$, 3H), 4.85 t (H-1 1H).

Calcd for $C_9H_{18}N_2O_4$: C, 49.53; H, 8.31; N, 12.84. Found: C, 49.26; H, 8.11; N, 12.63.

Methyl 2,3,6-trideoxy-3-(3-methyl-3-nitrosoureido-α-L-lyxo-hexopyranoside.

Methyl 2,3,6-trideoxy-3-methylureido-α-L-lyxo-hexopyranoside (5.4 g, 25 mmoles) was nitrosated with about 45 mmoles of $N_2O_3$ added in 3 portions at 0°. After 8 hours, the mixture was lyophilized, the residue dissolved in chloroform, and the solution dried over magnesium sulfate. Evaporation of the solvent left a residual syrup which crystallized upon trituration with ether to give 2.9 g, mp 97°–99°; a second crop was obtained by recrystallization of the mother liquid from ether/chloroform/methanol to give a total of 3.0 g (48%); ir ($\mu$): 2.85, 2.95 (OH, NH), 5.8 (C=O), 6.55 (amide II); nmr ($\delta$) ($CDCl_3$): 1.28 d ($CCH_3$, 3H), 1.8-2.2 m (H-2, 2H), 3.18 s ($NCH_3$, 3H), 3.4 s ($OCH_3$, 3H), 4.8 t (H-1, 1H); tlc: $R_f$ 0.7.

Calcd for $C_9H_{17}N_3O_5$: C, 43.72; H, 6.93; N, 17.0. Found: C, 43.81; H, 7.04; N, 16.85.

The solid was stable when stored for several weeks at room temperature, but had decomposed after 8 months.

EXAMPLE 5

Methyl 3-Deoxy-3-(3-methyl-3-nitrosoureido)-α-D-glucopyranoside (V)

Methyl 4,6-O-benzylidene-3-deoxy-3-(3-methylureido)-α-D-glucopyranoside.

A solution of 5.6 g (20 mmol) of methyl 3-amino-4,6-O-benzylidene-3-deoxy-α-D-glucopyranoside, Guthrie and Johnson, J. Chem. Soc., 4166 (1961), in 15 ml of water and 50 ml of tetrahydrofuran was chilled to 0°. To the cold, stirred solution 1.4 ml (24 mmol) of methyl isocyanate was added in two portions over 10 min. A solid precipitated almost immediately from the reaction solution. The mixture was diluted with 50 ml of tetrahydrofuran and the slurry was stirred for 45 min. at room temperature. The white solid (product) was filtered and then triturated thoroughly with approximately 35 ml of $CHCl_3$ to wash out impurities. The amorphous white solid was air dried to give 5.1 g (76%) of an analytically pure product, m.p. 277°–287°; ir 3.0 (OH, NH), 6.05 (C=O), 6.3 $\mu$, tlc on silica gel, $R_f$ 0.45 in methanol-benzene (1:4).

Methyl 3-deoxy-3-(3-methylureido)-α-D-glucopyranoside. Methyl 4,6-O-benzylidene-3-deoxy-3-(3-methylureido)-α-D-glucopyranoside (11.0 g, 32.5 mmol) was suspended in 20 ml of tetrahydrofuran and 100 ml of water along with 30 g of Dowex 50X-8 (H) (prewashed with THF-water). The reaction mixture was stirred at room temperature for 15 hours to give a clear solution. The resin was filtered and washed with THF-water. The filtrate was concentrated until all the THF was removed. The residual aqueous solution was extracted with two 100-ml portions of dichloromethane to remove benzaldehyde. The aqueous layer was filtered through Celite and then evaporated to yield 6.2 g (76%) of a glassy solid; ir 6.13 (C=O), 6.30 $\mu$; nmr (DMSO-$d_6$) $\delta$4.63 d (H.1, $J_{1,2}$ = 3.5 Hz), 3.35 s ($OCH_3$), 2.60 s ($NCH_3$); tlc on silica gel, $R_f$ 0.2 in methanol-benzene (1:4). This material was used in the next step. A sample (0.80 g) was recrystallized from 10 ml of isopropanol to give an analytical sample (0.62 g), which was dried in vacuo at 100°, m.p. 171°–172°.

Methyl 3-deoxy-3-(3-methyl-3-nitrosoureido-α-D-glucopyranoside.

Methyl 3-deoxy-3-(3-methylureido-α-D-glucopyranoside (6.0 g, 24 mmol) was dissolved in 75 ml of water. The solution was chilled at 0°, and then liquid dinitrogen trioxide was added dropwise (approximately 2.5–3.0 ml) until a permanent reaction to starch iodide test paper was obtained. It was stirred at 0° for 4 hours, and at room temperature 1 hour. The reaction mixture was still positive to starch iodide paper. The aqueous solution was filtered and then lyophilized overnight to yield 7.6 g of a yellow foamed glass (still wet, theor. yield 6.7 g); ir 5.82 (C=O), 6.48 $\mu$; nmr (DMSO-$d_6$, internal TMS) $\delta$ 4.68 d (H.1, $J_{1,2}$ = 3.3 Hz), 3.37 s ($OCH_3$), 3.13 s ($NCH_3$); tlc on silica gel, $R_f$ 0.45 in methanol-benzene (1:4) with a trace spot at $R_f$ 0.20 indicative of starting material. Small amounts of starting material would have been missed in the nmr run in DMSO-$d_6$, owing to interference from the solvent peak near $\delta$ 2.60.

An acetone solution of the product was dried over $MgSO_4$ and evaporated to give 6.9 g (nmr disclosed the presence of 10% acetone). Several attempts at recrystallization were unsuccessful. Finally, the various fractions were combined (4.7 g) and retreated as before with liquid $N_2O_3$. After 5 hrs at 0°, the reaction solution was still positive to starch iodide test paper and was lyophilized. When a small portion of the residue (5.9 g) was dissolved in water, it was still positive to starch iodide and gave a pH of 2. The residue was dissolved in acetone and evaporated; this was repeated (three times) until the residue was negative to starch iodide. It was then dissolved in water and lyophilized to give 3.8 g of a dry and grainy, pale yellow solid that analyzed as the hemihydrate ($C_9H_{17}N_3O_7\cdot\frac{1}{2}H_2O$). The nmr in $D_2O$ (external TMS) showed no starting material at $\delta$ 2.70 (less than 2%); $\delta$ 4.87 d ($J_{1,2} = 3.5$ Hz), 3.48 s ($OCH_3$), 3.13 s ($NCH_3$). The tlc on silica gel was homogeneous (very faint spot suggested the possibility of a trace of starting material). The solution for nmr was stored for 10 days at 0° without decomposition.

In connection with the data presented above, it may be noted that melting points were observed on a Fisher-Johns hot stage and are uncorrected. Infrared spectra were determined routinely in Nujol mull (solids) or as a liquid film. Pmr spectra were determined on a Varian A-60A spectrometer in $CDCl_3$ solution with $Me_4Si$ as internal reference ($\delta = 0.0$), unless otherwise designated in DMSO (dimethyl sulfoxide-$d_6$, internal $Me_4Si$) or $D_2O$ (external $Me_4Si$). Signals are designated as s (singlet), doublet (d), triplet (t). Integrated peak ratios were as expected from the structure assignments. Thin-layer chromatography was done with silica gel HF (E. Merck) on 5 × 20 cm glass plates in MeOH—$C_6H_6$ (solvent ratios are given in parentheses following the $R_f$'s), unless the solvent is otherwise designated. Organic solutions were commonly dried over $MgSO_4$, and evaporations were carried out in vacuo.

BIOLOGICAL DATA

Preliminary evaluation of antitumor properties was done by Drug Research and Development, National Cancer Institute, according to its protocols, R. I. Geran, N. H. Greenberg, M. M. MacDonald, A. M. Schumacher, and B. J. Abbott, *Cancer Chemother. Rep.* (Part 3), 3 (no. 2, September 1972). Test results (T/C) for the five nitrosoureas against L1210 murine leukemia are listed below in Table I. Streptozotocin is active only on a daily treatment schedule, and just meets the minimum activity requirement in these tests for further development, J. M. Venditti, *Cancer Chemother. Rep.*, 2, 35 (no. 1, October 1971). In the three-injection regimen compounds I, II and V displayed substantial activity, in contrast to streptozotocin which is without effect. In the nine-injection schedule all of the new drugs except IV (not evaluated in this system) were active, including III which was not effective on the three-dose schedule. Compound V is clearly at least equal to the parent antibiotic, and xylose derivative I appears definitely superior, effecting cures in two out of six mice at 100 mg/kg. Altrose derivative II yielded T/C values too erratic to allow a clear comparison with streptozotocin.

Acute toxicity among the new drugs appear to be somewhat lower than that found for streptozotocin. None of the drugs assayed on the nine-injection regimen caused toxic deaths among test mice at 200 mg/kg, a level where streptozotocin begins to show this effect. At 400 mg/kg, I and III did cause one toxic death out of six animals, and three out of ten for V.

TABLE I

ANTITUMOR TEST RESULTS
L1210 lymphoid leukemia assay in mice[b]

| Structure No. | NSC[a] No. | 3 injections (IP) dose (mg/kg) | T/C(%)[c] | 9 injections (IP) dose (mg/kg) | T/C(%)[c] |
|---|---|---|---|---|---|
| I | 153365 | 400 | 162 | 400 | |
| | | 200 | 291 | 200 | 134 |
| | | 150 | 167 | 100 | 224(2 cures) |
| | | 100 | 160,145,136 | 75 | 186 |
| | | 66 | 135,138,126 | 50 | 160 |
| | | 44 | 126 | 33 | 135 |
| | | 33 | 118 | 22 | 141 |
| | | 27 | 112 | | |
| | | 16 | 108 | | |
| II | 156273 | 400 | 100 | | |
| | | 200 | 133 | 200 | 100 |
| | | 150 | 105,122 | 150 | 118,136 |
| | | 100 | 142,158,118 | 100 | 218,103,131 |
| | | 66 | 100,111 | 66 | 126,137 |
| | | | | 50 | 181 |
| III | 155692 | 400 | 107 | 400 | 119 |
| | | 200 | 100 | 300 | 105 |
| | | 100 | 94 | 200 | 129,198 |
| | | | | 132 | 151 |
| | | | | 100 | 124 |
| IV | 166643 | 500 | 101 | | |
| | | 400 | 133,106 | | |
| | | 200 | 110 | | |
| | | 100 | 111 | | |
| V | 160466 | 400 | 214 | | |
| | | 200 | 166,140 | 150 | 157 |
| | | 100 | 130,135 | 100 | 165,145 |
| | | 50 | 105,127 | 66 | 137 |
| | | 25 | 106 | 50 | 140 |
| | | | | 44 | 124 |
| | | | | 25 | 125 |
| | | | | 12.5 | 112 |
| Streptozotocin[d] | 85998 | 256 | <125 | 50[e] | 150 |

TABLE I-continued

ANTITUMOR TEST RESULTS
L1210 lymphoid leukemia assay in mice[b]

| Structure No. | NSC[a] No. | 3 injections (IP) dose (mg/kg) | T/C(%)[c] | 9 injections (IP) dose(mg/kg) | T/C(%)[c] |
|---|---|---|---|---|---|
| | | 32 | <125 | | |

[a]Accession number of the National Cancer Institute
[b]Tested by the Drug Research and Development Branch of the National Cancer Institute according to its protocols; Cancer Chemotherapy Reports, part 3, 3 (No. 2, September 1972)
[c]A T/C ration ≥ 125% is a positive result denoting activity.
[d]Data from John M. Venditti, Cancer Chemotherapy Reports, part 3, 2, 35 (No. 1, October 1971).
[e]Optimum dose.

What is claimed is:

1. The 3-methyl-3-nitrosoureido derivatives of the following amino sugars: methyl 3-amino-3-deoxy-β-D-xylopyranoside; methyl 3-amino-3-deoxy-α-D-altropyranoside; 3-amino-3-deoxy-1,2-O-isopropylidene-α-D-ribofuranose; methyl 3-amino-2,3,6-trideoxy-α-L-lyxohexopyranoside; and methyl 3-amino-3-deoxy-α-D-glucopyranoside.

2. The compound of claim 1 which is methyl 3-deoxy-3-(3-methyl-3-nitrosoureido)-β-D-xylopyranoside.

3. The compound of claim 1 which is methyl 3-deoxy-3-(3-methyl-3-nitrosoureido)-α-D-altropyranoside.

4. The compound of claim 1 which is 3-deoxy-1,2-O-isopropylidene-3-(3-methyl-3-nitrosoureido)-α-D-ribofuranose.

5. The compound of claim 1 which is methyl 2,3,6-trideoxy-3-(3-methyl-3-nitrosoureido)-α-L-lyxohexopyranoside.

6. The compound of claim 1 which is methyl 3-deoxy-3-(3-methyl-3-nitrosoureido)-α-D-glucopyranoside.

* * * * *